(12) United States Patent
Hsiao et al.

(10) Patent No.: US 8,889,853 B2
(45) Date of Patent: Nov. 18, 2014

(54) PROCESS FOR THE PREPARATION OF DISACCHARIDES APPLIED TO HEPARIN PENTASACCHARIDES

(75) Inventors: Tsung Yu Hsiao, Kaohsiung County (TW); Chen Wei Lin, Chiayi (TW)

(73) Assignee: Scinopharm Singapore Pte Ltd., Singapore (SG)

( * ) Notice: Subject to any disclaimer, the term of this patent is extended or adjusted under 35 U.S.C. 154(b) by 383 days.

(21) Appl. No.: 13/253,863

(22) Filed: Oct. 5, 2011

(65) Prior Publication Data

US 2012/0083594 A1 Apr. 5, 2012

Related U.S. Application Data

(60) Provisional application No. 61/389,844, filed on Oct. 5, 2010.

(51) Int. Cl.
| | | |
|---|---|---|
| *C07H 1/00* | (2006.01) | |
| *C07H 3/00* | (2006.01) | |
| *C08B 37/00* | (2006.01) | |
| *C07H 9/04* | (2006.01) | |
| *C07H 15/18* | (2006.01) | |
| *C07H 17/04* | (2006.01) | |

(52) U.S. Cl.
CPC .. *C07H 1/00* (2013.01); *C07H 9/04* (2013.01); *C07H 15/18* (2013.01); *C07H 17/04* (2013.01)
USPC ...................................................... 536/126

(58) Field of Classification Search
None
See application file for complete search history.

(56) References Cited

U.S. PATENT DOCUMENTS 4,818,816 A    4/1989  Petitou et al.

OTHER PUBLICATIONS

Greene & Wuts, Protective Groups in Organic Synthesis, Third Edition, John Wiley & Sons, Inc., New York, NY, 1999, only pp. 179-189 & 195 supplied, see "Carbonates" and "Carbamate," respectively.*
Li et al., "Synthetic Approaches to the 2002 New Drugs," Mini-Reviews in Medicinal Chemistry, 4, 207-233 (2004)).*
Van Boeckel, C. A. A. et al., "Synthesis of a Pentasaccharide Corresponding to the Antithrombin III Binding Fragment of Heparin" Journal of Carbohydrate Chemistry, (1985), 4(3): 293-321.
Takamura, T. et al., "Chemical Modification of Lactose. XI A New Synthesis of 2-Acetamido-2-deoxy-4-O-β-D-galactopyranosyl-α-D-glucopyranose (N-Acetylactosamine)" Chemical and Pharmaceutical Bulletin (1979), 27(3): 721,725.
Ichikawa, Y. et al., "Synthesis, From Cellobiose, of a Trisaccharide Closely Related to the GlcNAc-->GlcA-->GlcN Segment of the AntiThrombin-Binding Sequence of Heparin" Carbohydrate Research (1985), 141(2): 273-82.
Extended European Search Report issued on Feb. 28, 2014 for European counterpart application No. 11831015.0.
P. Duchaussoy et al., Bioorganic & Medicinal Chemistry Letters. vol. 1, No. 2, pp. 99-102.1991.
Ichikawa et al., Carbohydrate Research, 141 (1985) 273-282.
M. Petitou et al., Bioorganic & Medicinal Chemistry Letters, vol. 1,No. 2, pp. 95-98,1991.
Takamura et al., Chem Pharm Bull 27(3) 721-725, 1979.

* cited by examiner

*Primary Examiner* — Lawrence E Crane
(74) *Attorney, Agent, or Firm* — Enshan Hong; Kent H. Cheng; VLP Law Group LLP

(57)    ABSTRACT

The invention provides an intermediate and the process for making the same. This intermediate is useful in the process for making polysaccharides, and more particularly fondaparinux.

16 Claims, No Drawings

PROCESS FOR THE PREPARATION OF DISACCHARIDES APPLIED TO HEPARIN PENTASACCHARIDES

CROSS REFERENCE TO RELATED APPLICATIONS

The present application claims priority from U.S. Provisional Patent Application Ser. No. 61/389,844, filed on Oct. 5, 2010, the contents of which is herein incorporated by reference.

BACKGROUND OF THE INVENTION

1. Field of the Invention

The invention relates to a process of preparing the (B-C) disaccharide intermediate, a building block for the preparation of polysaccharides, and more particularly fondaparinux.

2. Description of the Related Art

Fondaparinux (A-B-C-D-E) is a heparin sulfated pentasaccharide with anticoagulant activity and a linear sequence is required for binding to antithrombin III (ATIII). Because fondaparinux is a synthetic compound, it is considered a safer medication than the traditional anticoagulant, heparin or LMWH (low-molecular-weight heparin).

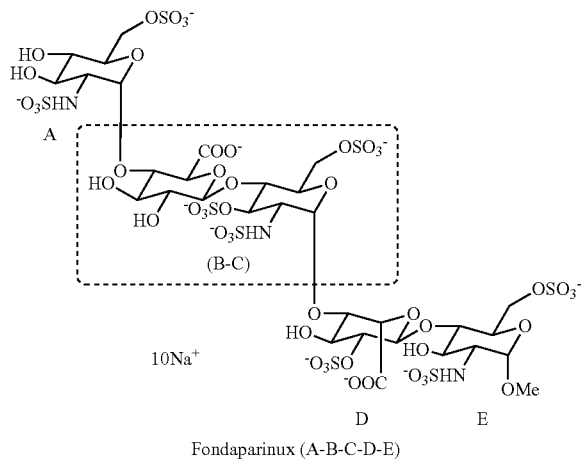

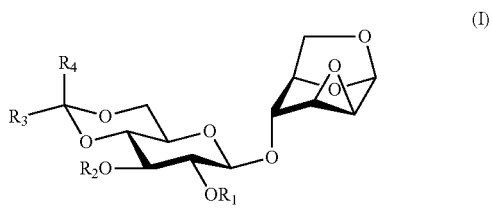

Fondaparinux (A-B-C-D-E)

U.S. Pat. No. 4,818,816 discloses processes for preparing the (B-C) disaccharide building block of fondaparinux. However, the selectivity is not good enough and the compound needs to be purified by column chromatography, which is not suitable for use in an industrial process.

SUMMARY OF THE INVENTION

The present invention provides a novel process for preparing the intermediate of the (B-C) disaccharide building block of fondaparinux (A-B-C-D-E). The selectivity of the process is 100%. In addition, the compound obtained by the process could be purified by crystallization. The present invention is more suitable for use in an industrial process.

The present invention provides a compound of formula (I)

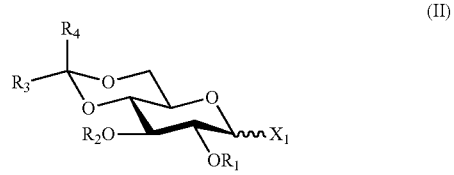

wherein
  $R_1$ is selected from the group consisting of alkylacyl, arylacyl and alkylarylacyl, or substituted alkylacyl, arylacyl and alkylarylacyl; carbonate, and carbamate;
  $R_2$ is an oxygen-protecting group;
  $R_3$ and $R_4$ are independently selected from hydrogen, methyl, $C_2$-$C_5$ alkyl, phenyl and aryl.

Compound (I) above can be used in preparing the intermediate of B-C disaccharide building block of fondaparinux.
Preferably, $R_1$ is benzoyl.
Preferably, $R_2$ is selected from the group consisting of 4-methoxyphenyl; benzyl, substituted benzyl; alkylacyl, arylacyl and alkylarylacyl, or substituted alkylacyl, arylacyl and alkylarylacyl; and carbonate.

The present invention also provides a process for preparing the compound of formula (I) by glycosylation of compound of formula (II)

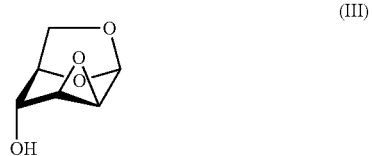

with the compound of formula (III)

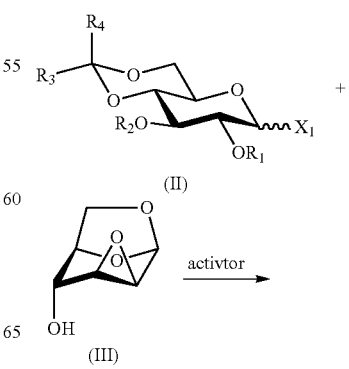

wherein
  $R_1$, $R_2$, $R_3$ and $R_4$ are as defined for compound of formula (I); and
  $X_1$ is a leaving group.

Preferably, $X_1$ is selected from thioalkyl, thioaryl, halogen, imidoyl, 4-penten-1-yloxy and the stereochemistry may be alpha or beta. More preferably, $X_1$ is thiocresyl.

The above glycosylation is preferably conducted in the presence of an activator and a solvent. Preferably, the activator is a sulfonic acid, sulfonate, silyl sulfonate, N-iodosuccinimide (NIS), or a mixture thereof, more preferably, the activator is NIS, trifluoromethanesulfonic acid (TfOH), or Trimethylsilyl triflate (TMSOTf). Preferably, the solvent is an aprotic solvent, and more preferably the solvent is dichloromethane (DCM) and acetonitrile (ACN).

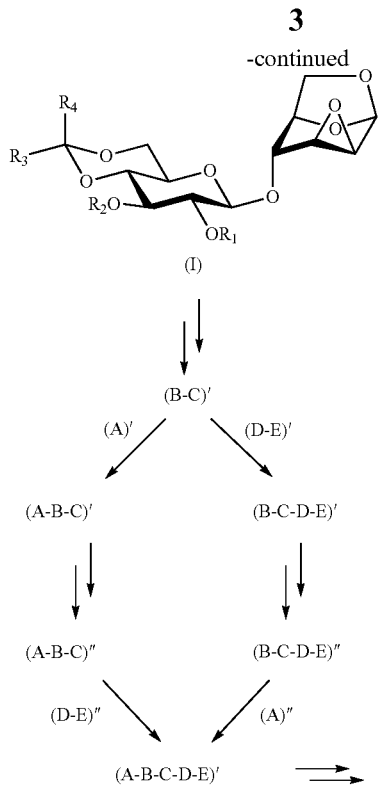

(I)

(B-C)'
(A)'     (D-E)'

(A-B-C)'    (B-C-D-E)'

(A-B-C)"    (B-C-D-E)"

(D-E)"      (A)"

(A-B-C-D-E)' ⟶ Fondaprinux

Compound (I) can be used for preparing (B-C)' disaccharide. (B-C)' disaccharide can be applied for preparing polysaccharides generally, and more particularly, fondaparinux by using the "BC+A+DE" or "BC+DE+A" synthetic strategy where (B-C)', (B-C)", (D-E)' and (D-E)" represent the β-anomeric disaccharides.

The present process has several advantages: (1) higher efficiency in the glycosylation of compound (II) and (III) (high yield and exclusive stereoselectivity), as only β-anomeric disaccharide is produced; (2) a convenient synthetic process from compound (I) to (B-C)'; (3) the preparation of compound (II) is easier than the method disclosed in U.S. Pat. No. 4,818,816; (4) less protecting groups on the C unit are used, resulting in less waste.

EXAMPLES

Example 1

Synthesis of (Ia) from (IIa)

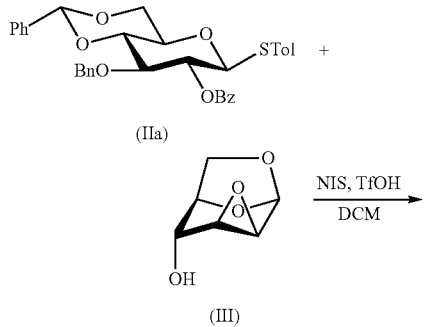

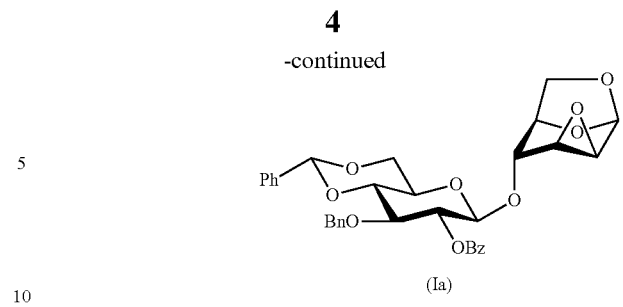

Charged (IIa) (7.65 g, 1.2 eq.), (III) (1.62 g, 1 eq.) and molecular sieve (MS, 3 g, 1 part) in dry DCM (50 mL, 5 part), the mixture was stirred for 30 min. To the reaction mixture is added N-iodosuccinimide (NIS) (15.6 g, 1.1 eq.) and the mixture was cooled to −40° C., and TfOH (0.4 mL, 0.2 eq.) was added. The reaction mixture was stirred at −50~−40° C. for 1 hr. After the reaction was finished, Et$_3$N (0.4 mL) was added and stirred for 10 min. The reaction mixture was filtered and washed with DCM (14 mL, 5 part). The filtrate was washed with 10% Na$_2$S$_2$O$_3$$_{(aq)}$ (4 part), and concentrated. Crystallization from DCM/n-heptane gave (Ia) (5.7 g, 87%)

Example 2

Synthesis of (Ic) from (Ia)

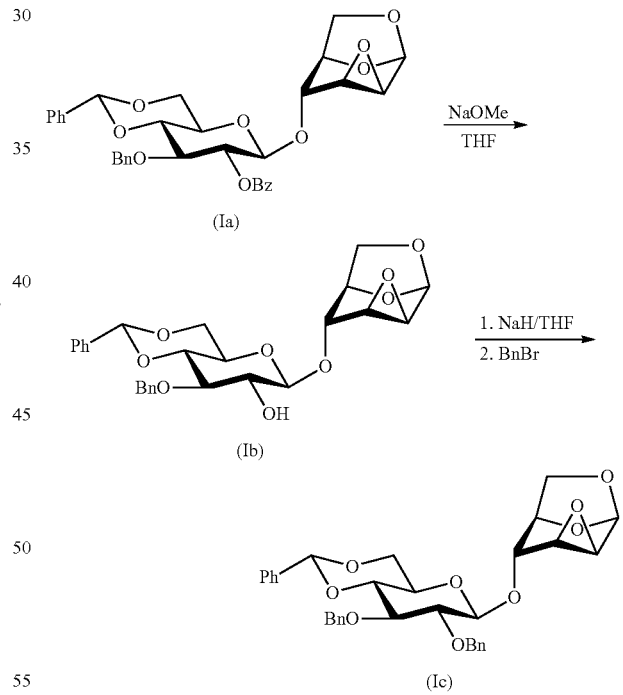

Charged (Ia) (9.0 g, 1 eq.) in THF (45 mL, 5 part) and added 30% NaOMe solution (4.1 mL, 1.5 eq.). The mixture was stirred for 30 min at 4~6° C. After the reaction was completed, the mixture was added to amberlite to neutralize the solution and remove solvent to afford the oily intermediate (Ib). After washed by NaCl$_{(aq)}$, the (Ib) was dissolved in THF and cooled to 0~5° C. and added NaH (1.83 g of a 60% suspension in oil, 3 eq.), TBAI (0.56 g, 0.1eq.). The mixture was stirred for 10 min and benzyl bromide (4.5 mL, 2.5eq.) was added. The mixture was stirred for 3 h at rt, water was added, and the mixture was evaporated. Extraction with DCM and crystallization from DCM/n-heptane gave (Ic) (7.1 g, 80%).

Example 3

Synthesis of (Ie) from (Ic)

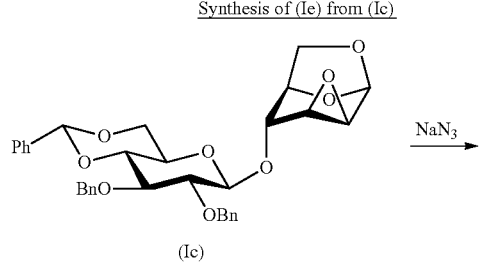
(Ic)

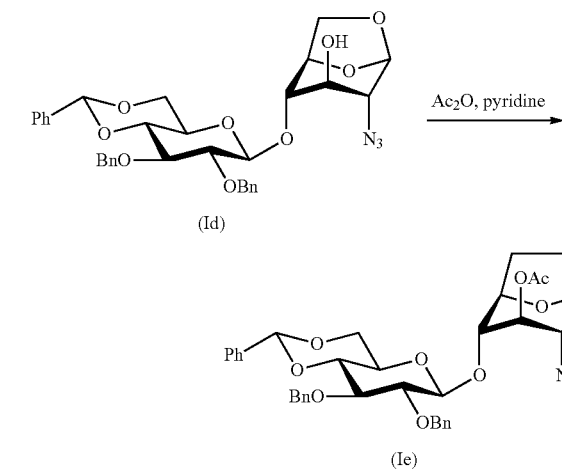

Charged (Ic) (7.0 g, 1 eq.) in DMF/H$_2$O (10/1 mL) and added NaN$_3$ (4.0 g, 5 eq.). The mixture was stirred for 24 hr at 120° C. After the reaction was completed, the mixture was extracted with ethyl acetate. The organic layer was evaporated to afford crude (Id). Then, crude (Id) was dissolved in pyridine (6 mL, 0.8 part) and added Ac$_2$O (3 mL, 0.4 part). The mixture was stirred for 16 hr at rt. After the reaction was completed, the mixture was extracted with ethyl acetate and washed by NaHCO$_3{}_{(aq)}$. The solvent of pyridine was co-evaporated with toluene three times. The organic phase was concentrated and the residue was purified by column chromatography to give (Ie) (6.3 g, 78%).

Example 4

Synthesis of (If) from (Ie)

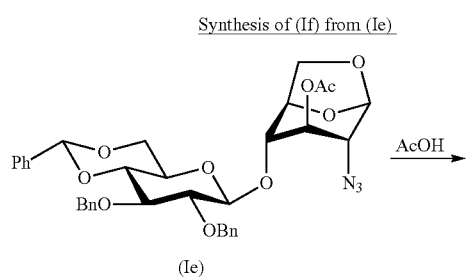
(Ie)

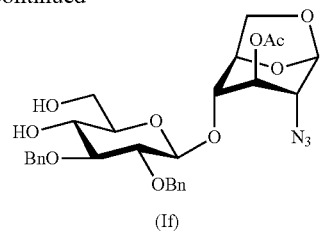
(If)

Charged (Ie) (6.3 g, 1 eq.) in 80% AcOH$_{(aq)}$ (60 mL). The mixture was stirred for 5 hr at 70° C. After the reaction was completed, the solvent was removed by vacuum. The mixture was extracted with ethyl acetate and washed by NaHCO$_3{}_{(aq)}$. The organic layer was concentrated and the residue was purified by column chromatography to give (If) (5.3 g, 97%).

Example 5

Synthesis of (Ih) from (If)

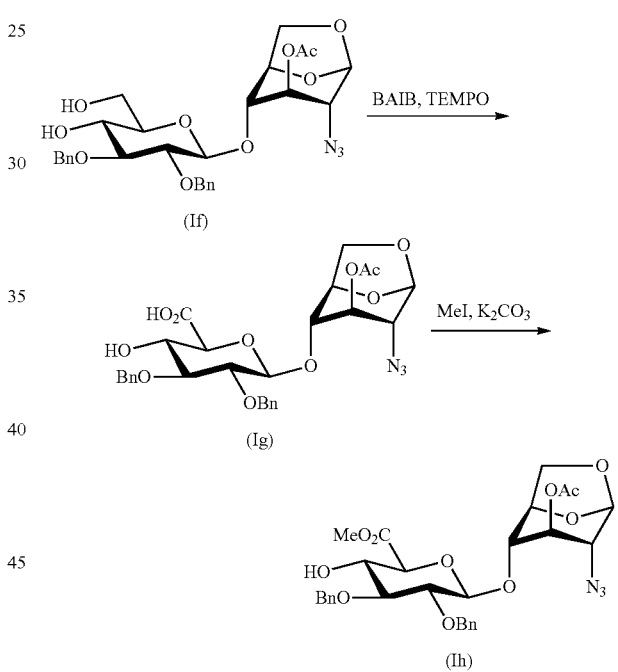

Charged (If) (4.0 g, 1 eq.) in DCM/H$_2$O (40/20 mL) and added 2,2,6,6-tetramethylpiperidine-1-oxyl (TEMPO) (220 mg, 0.2 eq.) and [bis(acetoxy)iodo]benzene (BAIB) (6.8 g, 3 eq.). The reaction mixture was stirred at room temperature for 1 hr. The reaction was monitored by TLC. After the reaction was finished, the reaction mixture was washed with 10% Na$_2$S$_2$O$_3{}_{(aq)}$ and extracted with ethyl acetate. The organic layer was concentrated to give the acid intermediate (Ig) without further purification. Then, charged crude (Ig) in DMF (40 mL) and added K$_2$CO$_3$ (660 mg, 0.64 eq.) and MeI (1.1 mL, 2.5 eq.). The reaction mixture was stirred at room temperature for 16 hr. The reaction was monitored by TLC. After the reaction was finished, the reaction mixture was extracted with ethyl acetate and washed by NaCl$_{(aq)}$. The organic layer was concentrated and the residue was purified by column chromatography to give (Ih) (3.4 g, 80%).

We claim:
1. A process for preparing a compound of formula (I)

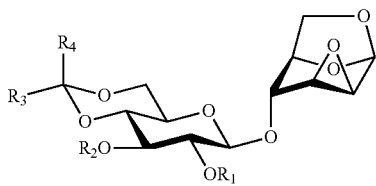

comprising the step of:
the glycosylation of compound of formula (II)

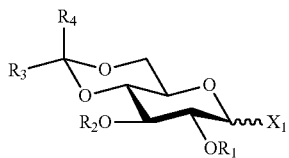

with a compound of formula (III)

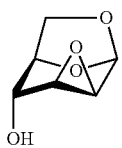

wherein
$R_1$ is selected from the group consisting of benzyl, alkylacyl, arylacyl, alkylarylacyl, substituted alkylacyl, substituted arylacyl, substituted alkylarylacyl, carbonate and carbamate;
$R_2$ is benzyl or another oxygen-protecting group;
$R_3$ and $R_4$ are independently selected from hydrogen, methyl, $C_2$-$C_5$ alkyl, and aryl; and
$X_1$ is a leaving group.

2. The process of claim 1, wherein $R_2$ is selected from the group consisting of 4-methoxyphenyl; benzyl, substituted benzyl; substituted benzyl, alkylacyl, arylacyl, alkylarylacyl, substituted alkylacyl, substituted arylacyl substituted alkylarylacyl and carbonate.

3. The process of claim 1, wherein $R_1$ is selected from the group consisting alkylacyl, arylacyl, alkylarylacyl, substituted alkylacyl, substituted arylacyl and substituted alkylarylacyl.

4. The process of claim 3, wherein $R_1$ is benzoyl.

5. The process of claim 1, wherein $X_1$ is selected from the group consisting of thioalkyl, thioaryl, halogen, imidoyl, and 4-penten-1-yloxy.

6. The process of claim 1, wherein $X_1$ has anomeric stereochemistry that is alpha or beta.

7. The process of claim 1, wherein $X_1$ is thiocresyl.

8. The process of claim 1, further comprising wherein the glycosylation is conducted in the presence of an activator.

9. The process of claim 8, wherein the activator is selected from the group consisting of sulfonic acids, sulfonate salts, silyl sulfonates, N-iodosuccinimide (NIS), and mixtures thereof.

10. The process of claim 9, wherein the activator is NIS, trifluoromethanesulfonic acid (TfOH), or trimethylsilyl triflate (TMSOTf).

11. The process of claim 1, wherein the glycosylation is conducted in the presence of a solvent.

12. The process of claim 11, wherein the solvent is an aprotic solvent.

13. The process of claim 11, wherein the solvent is dichloromethane (DCM) or acetonitrile (ACN).

14. The process of claim 1 further comprising converting the compound of formula (I) to a polysaccharide.

15. The process of claim 1 further comprising converting the compound of formula (I) to fondaparinux (A-B-C-D-E).

16. The process of claim 1, wherein $R_1$ is benzoyl, $R_2$, is benzyl, $R_3$ is phenyl and $R_4$ is hydrogen.

* * * * *